US00PP17741P3

(12) United States Plant Patent
Fotinos

(10) Patent No.: US PP17,741 P3
(45) Date of Patent: May 15, 2007

(54) *HYDRANGEA* PLANT 'HYDONE'

(50) Latin Name: *Hydrangea macrophylla*
Varietal Denomination: HYDone

(76) Inventor: Peter Fotinos, 905 S. Patterson Ave., Santa Barbara, CA (US) 93111

( * ) Notice: Subject to any disclaimer, the term of this patent is extended or adjusted under 35 U.S.C. 154(b) by 9 days.

(21) Appl. No.: 11/073,478

(22) Filed: Mar. 7, 2005

(65) Prior Publication Data

US 2006/0200882 P1 Sep. 7, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—Annette H Para

(57) ABSTRACT

A new *Hydrangea* plant, which has abundant, rose-green or blue-green colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

5 Drawing Sheets

Latin name of genus and species: *Hydrangea macrophylla* 'HYDone'.

Variety denomination: The new variety is named 'HYDone'.

BACKGROUND OF THE INVENTION

The present invention constitutes a new and distinct variety of *Hydrangea* plant, which was developed by artificially pollinating an unnamed seedling (not patent in the US) with an unnamed seedling (not patent in the US). The two parents were crossed in the spring of 2002 and the resulting seed was sown in September 2002, in a controlled glasshouse environment. Out of these seedlings one seedling was selected, as the new variety and named 'HYDone'. The new *Hydrangea* plant may be distinguished from its seed parent, an unnamed seedling, by the following combination of characteristics:

1. The unnamed seedling has a breeding background in unnamed seedlings.
2. 'HYDone' has medium dome-shaped inflorescences, while the unnamed seedling has large dome-shaped inflorescences.
3. 'HYDone' has rose-green or blue-green colored flowers, while the unnamed seedling has white flowers.

The new variety may distinguished from its pollen parent, an unnamed seedling created by the same inventor, by the following combination of characteristics:

1. The unnamed seedling has a breeding background in unnamed seedlings.
2. 'HYDone' has medium dome-shaped inflorescences, while the unnamed seedling has small flat inflorescences.
3. 'HYDone' has rose-green or blue-green flowers, while the unnamed seedling has red flowers.

BRIEF SUMMARY OF THE INVENTION

Initial asexual reproduction of 'HYDone' by cuttings was first done in Santa Barbara, Calif., USA. The reproduction was conducted in controlled greenhouse environments.

Have here proven that the foregoing and all after characteristics and distinctions to come true to form and are established in succeeding propagations.

'HYDone' is a low and compact *Hydrangea* plant with good vigor.

The objective of the hybridization of this *Hydrangea* variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and distinguish 'HYDone' from all other varieties of which we are aware.

The seeds, from hybridization were planted in a controlled environment and evaluations were conducted on the resulting plants. 'HYDone' was selected by Peter Fotinos, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'HYDone'. Specifically illustrated in:

Photo sheet 1:

1: Development of Pink flowers.
2: Developments of blue flowers.
3: Tip of young shoot.
4: Mature leaf, upper side.
5: Mature leaf, reverse side.

Photos sheet 2:

6: Bare stem with fully unfolded flower head.

7: Corymb with flowers detached.

Photo sheet 3:

8: Corymb starting to unfold, side view.

9: Corymb viewed from top, half unfolded.

Photo sheet 4:

10: Corymb viewed from top, fully unfolded.

Photo sheet 5:

11: Selection of pink flower.

12: Selection of blue flowers.

DETAILED BOTANICAL DESCRIPTION OF THE VARIETY

The following is a detailed description of the *Hydrangea* plant: *Hydrangea macrophylla* 'HYDone'.

The following observations, measurements, values and comparisons describe plants grown in glass houses in Santa Barbara, Calif., USA.

The age of the observed plants where 29 to 33 weeks after propagation by cuttings, and produced as flowering pot plants in container of 10 centimeter in diameter.

Environmental conditions in the cultivation area for the observed plants, has been temperatures from 36 to 78 degree Farenheit, and 10 to 20 hours day length with assimilation light. Light levels from 600 foot candle to 6000 foot candle. The relative humidity has been ranging from 50 to 85%. Plants have been regulated with Bonzi to modify the plant shape described.

Color references are made using The Royal Horticultural Society (London, England) Colour Chart, 1995, except where common terms of color are used. For a comparison, the nearest existing *Hydrangea* variety is 'Hobella', a *Hydrangea* variety described and illustrated in U.S. Plant Pat. No. 9,462. Chart 1 details several physical characteristics of 'HYDone' and 'Hobella'.

CHART 1

| | 'HYDone' | 'Hobella' |
|---|---|---|
| Sepal color, Upper surface | Red-Purple Group 64A w. Greyed-Green 194A or Blue Group 104C Greyed-Green 194A | Red-Purple Group 60A To 73D |
| Sepal color, Reverse surface | Red-Purple Group 64A w. Greyed-Green 194A or Blue Group 104C Greyed-Green 194A | Red-Purple Group 60A to 73D |
| Petal count | 4 | 4 |

Parents: Unnamed seedling. Times. Unnamed seedling.

Classification:

*Botanical.*—*Hydrangea macrophylla.*

*Commercial.*—Pot *Hydrangea.*

Plant:

*Plant growth.*—Moderately vigorous. Grows compact upright to bushy. When grown as 11 cm pot plant, the average height of the plant itself is 20 to 22 cm, and average width is 21 cm. When grown as a 16 cm pot plant, the average height of the plant itself is 24 to 36 cm, and average width is 30 cm. Production time is generally 29 to 33 weeks depending on average temperature, light level, and cultural practices. To create pink flower heads the plants was grown at pH 6.0. To create blue flower heads the plants was grown at pH 4.5 and Aluminum at 20 ppm was added to the irrigation water.

Stem:

*Color.*—Young wood: Yellow-Green Group 148A–B. Older wood: Yellow-Green Group 148B, with intonations of Red-Purple Group 187A, at the internode base.

*Lenticels.*—Incidence: 20–25 per internode. Size: 0.3–0.5 mm. Color: Greyed-Brown Group 200B. Shape: Round to ovate.

*Surface.*—Young wood: Smooth. Older wood: Smooth.

*Stem diameter.*—4–5 mm.

*Internode length.*—20–30 mm.

*Numbers of internodes.*—3–4.

Plant foliage: Leaves arranged alternately, generally symmetrical, abundant, and flat in aspect. The venation pattern is pinnate.

*Quantity of leaves.*—3 to 4 per lateral branch.

*Petioles.*—Color: Yellow-Green Group 147C. Margins: Entire. Length: 12–18 mm. Diameter: about 3–4 mm.

*Leaves.*—Edge: Serrated. Serration: Single. Shape: Ovate with acuminate apex and obtuse to acuminate base. Texture: Coriaceous. Appearance: Dull. Size: Length: 70 to 140 mm. Width: 35 to 50 mm. Color: Young foliage: Upper surface: Yellow-Green Group 147A. Lower surface: Greyed-Green Group 191B. Color: Mature foliage: Upper surface: Yellow-Green Group 147A. Lower surface: Greyed-Green Group 191A. Leaf vein color: Upper surface: Greyed-Green Group 192D. Reverse surface: Greyed-Green Group 190D.

Inflorescence:

*Blooming habit.*—Seasonal.

*Flower type.*—Single flowers densely arranged on a corymb spherical formed head. Corymb size: 10–15 cm in diameter. Arrangement: Pedicels of the sterile flowers are longer than the pedicels of the fertile flowers so that the fertile flowers are below the sterile flowers in the flower head. Fertile Flowers: 5–10 per flower head, with 4 petals. Sterile flowers: 30–40 with per flower head, with 4–8 sepals per flower.

*Peduncle.*—Color: Yellow-Green Group 148-C, with intonations of Grey-Purple Group 187A. Texture: Smooth, with lenticels. Length: 20–30 mm Diameter: 2–3 mm. Strength: Erect, strong. Count: 3–4 per stem.

*Pedicel.*—Color: Red-Purple Group 65B–C, Texture: Smooth. Length: 15–25 mm. Diameter: 1–2 mm. Count: 8–10 per peduncle. Strength: Erect, strong.

*Sterile flower.*—Form: Shape of flower when viewed from the side. Up on opening: Cupped. Open flower: Flat. Size: 25–35 mm in diameter. Sepals: 4–8 per sterile flower, Sepal size: Length: 15 to 30 mm. Width: 15 to 30 mm. Sepal shape: Orbicular with emarginated tip. Texture: Smooth. Margin: Entire. Appearance: Dull. Color: At emerging flower head Upper surface: At pH 6.0: Greyed-Green Group 194A, with intonations of White Group 155C. At pH 4.5: White Group 155C, with intonations of Greyed-Green Group 194A. Reverse surface: Upper surface: At pH 6.0: Greyed-Green Group 194A, with intonations of White Group 155C. At pH 4.5: White Group 155C, with intonations of Greyed-Green Group 194A. Full unfolded flower head Upper surface: At pH 6.0: Red-Purple Group 65A–D most at the center. Following the veins to the edge. Intonations of White Group 155B. At pH 4.5: Blue Group 104C–d most at the center, following veins to the edge. Intonations of White Groups 155B emerging from the edge. Intonations of Red-Purple Group 74D occurring from center to the base. Reverse surface: At pH 6.0: Red-Purple Group 65A–D most at the center. Following the veins to the edge. Intonations of White Group 155B. At pH 4.5: Blue Group 104C–D most at the center, following veins to the edge. Intonations of White Groups 155B emerging from the edge. Intonations of Red-Purple Group 74D on the veins.

*Eye.*—Color: At pH 6.0: Greyed-Green Group 194A, change to Red-Purple Group 65A. At pH 4.5: Greyed-Green Group 194A, change to Blue Group 104B–C. Size: 2–3 mm in diameter.

*Fertile flower.*—Size: 3–5 mm in diameter. Form: Shape of flower when viewed from the side. Up on opening: Cupped. Open flower: Cupped.

*Color.*—Petals, upon opening. Upper surface: At pH 6.0: Red-Purple Group 65A Group At pH 4.5: Blue Group 104B–C. Reverse surface: At pH 6.0: Red-Purple Group 65B Group At pH 4.5: Blue Group 104C–D. Petals after opening: Upper surface: At pH 6.0: Red-Purple Group 65A Group At pH 4.5: Blue Group 104B–C. Reverse surface: At pH 6.0: Red-Purple Group 65B Group At pH 4.5: Blue Group 104C–D.

*Petals.*—Petal reflex. Outermost petals reflex inwards at opening. Fully open all petals reflex inwards. Texture. Smooth. Petal edge. Entire. Petal count. 4 per flower. Petal size. Length 3–5 mm Width: 2–3 mm. Shape. Round — ovate.

*Reproductive organs* (*only present on fertile flowers*).—Stamen number: 4 per flower. Anther shape: Two-lobed. Anther color: At pH 6.0: Red-Purple Group 65A Group. At pH 4.5: Blue Group 104B–C. Pollen amount: Scarce. Pollen color: White Group 155B. Filament: Color, White Group 155B. Length 1 mm. Pistils number: 4 per flower.

*Pistils.*—Stigma shape: Round. Stigma color: White Group 155A. Style: Color, White Group 155A. Length 1 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Santa Barbara, Calif. Seeds has not been observed due to that the plant has never been grown to the stage of seed development, due to the fact, that the variety is developed for use as a flowering pot plant only.

Winter hardiness & drought/heat tolerance: Due to the fact, that this variety is a potted flowering plant, developed indoor use only, the plant are not tested for winter hardiness or drought/heat tolerance.

It is claimed:

1. A new and distinct variety of *Hydrangea* plant, substantially as herein illustrated and described as a distinct and novel rose variety due to its abundant rose-green or blue-green flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

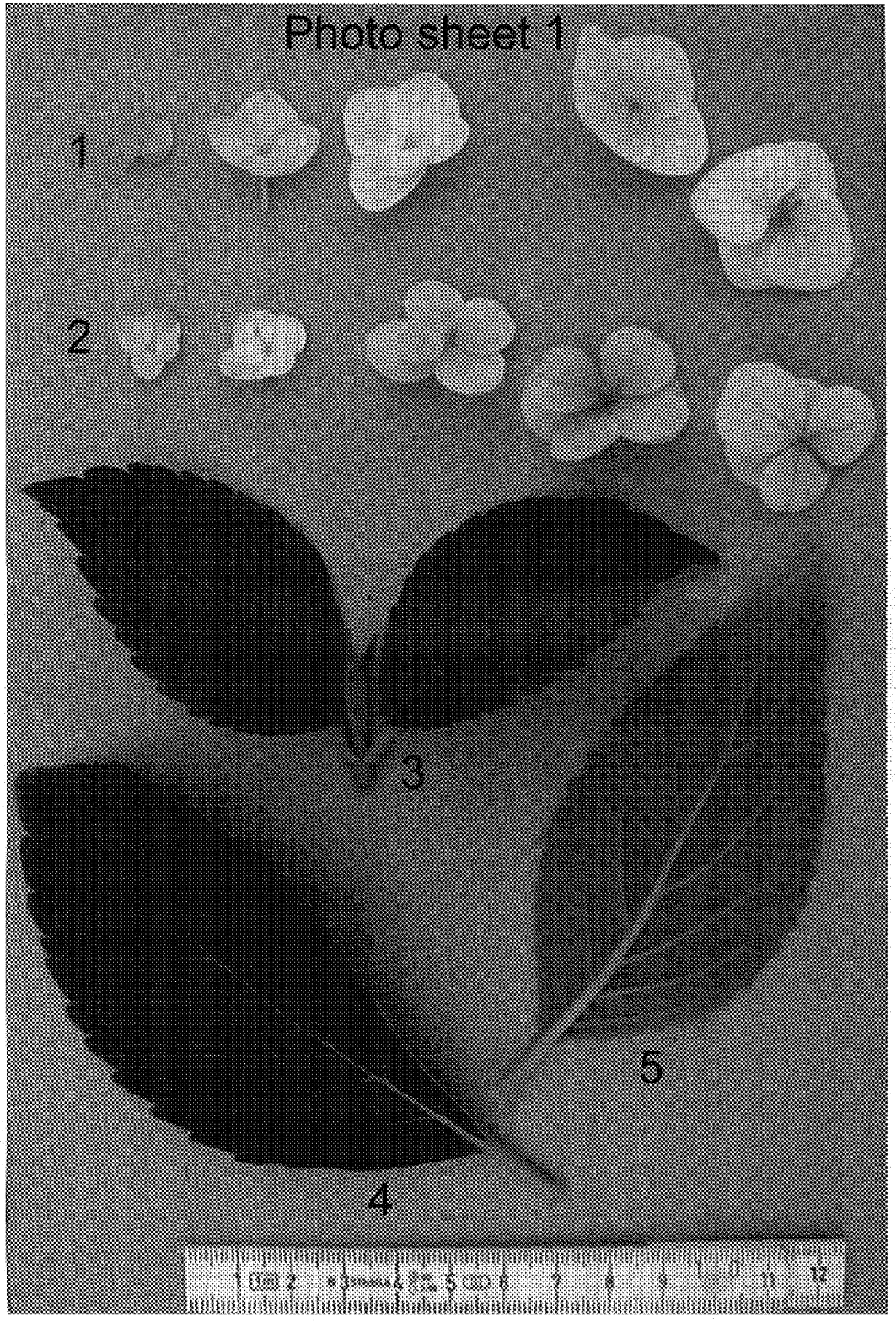
Photo sheet 1
1
2
3
4
5

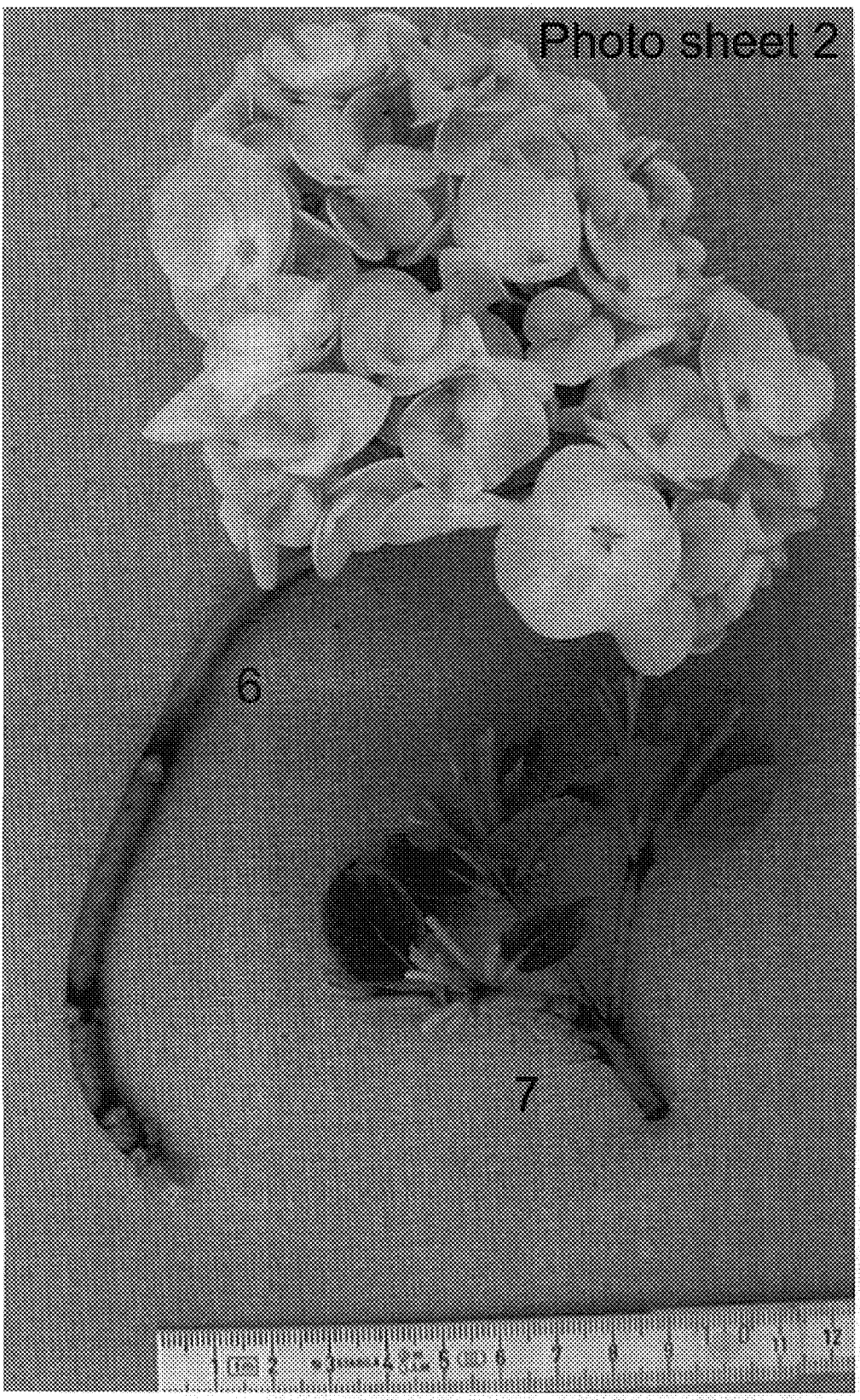
Photo sheet 2
6
7

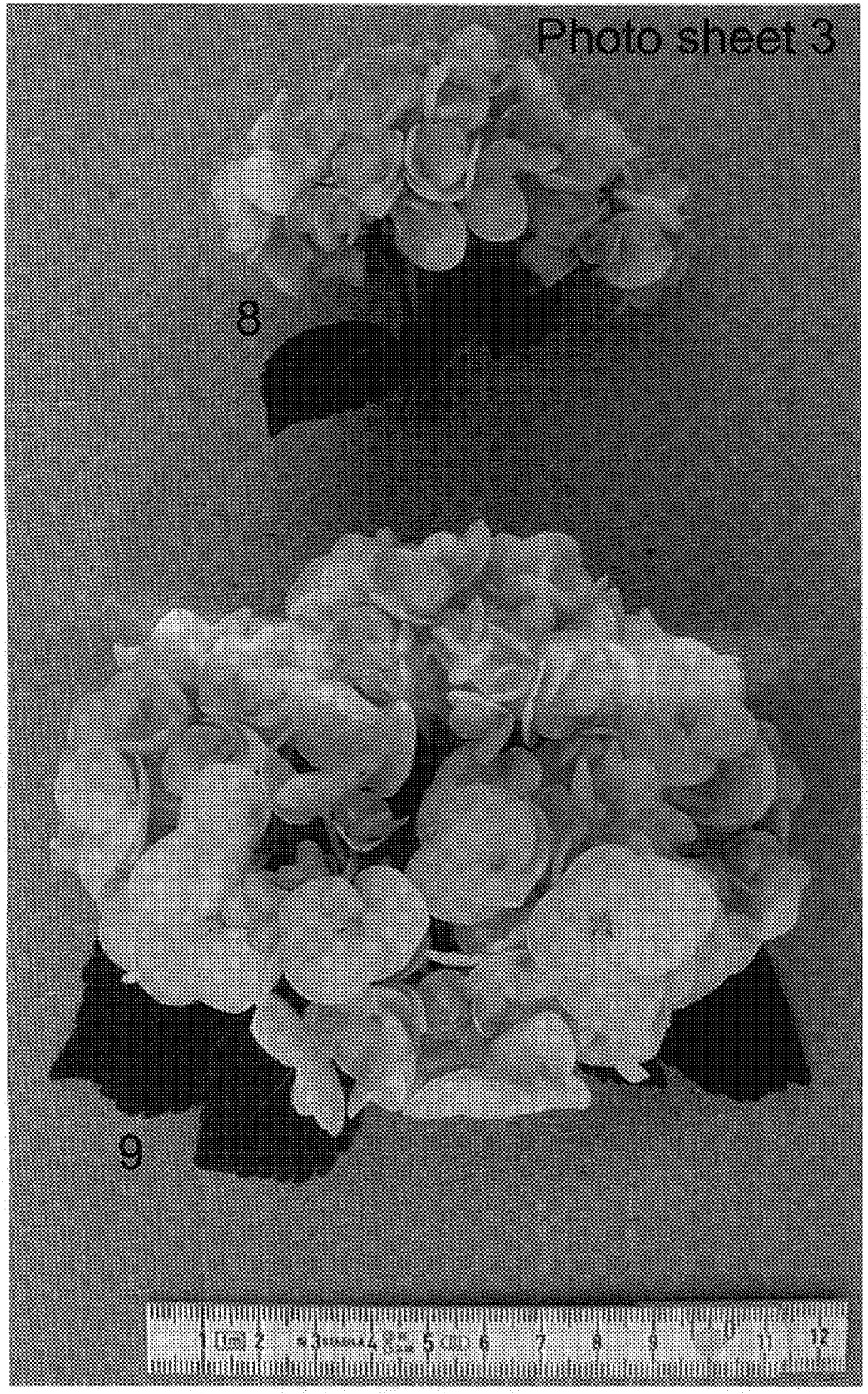
Photo sheet 3
8
9

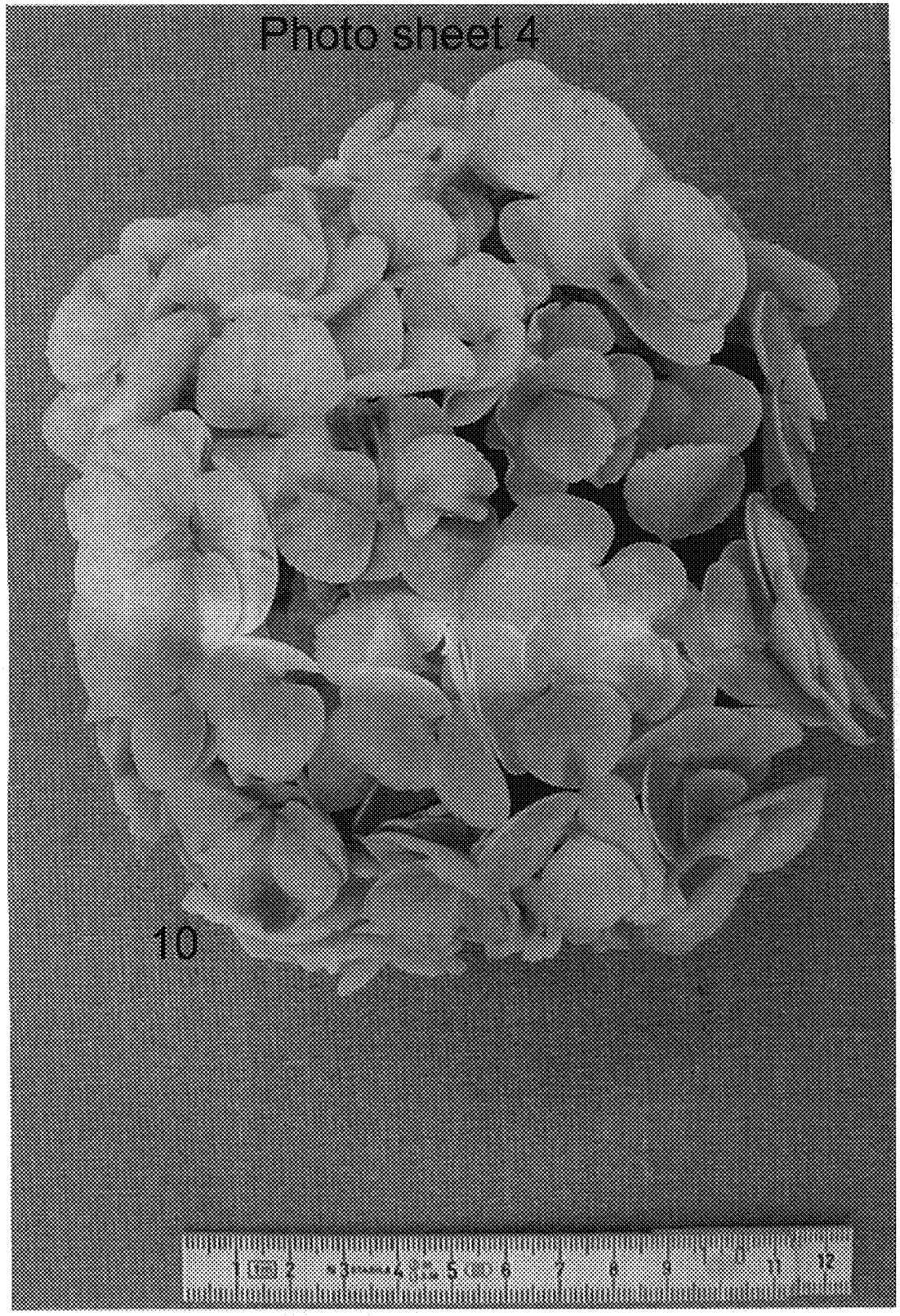
Photo sheet 4
10

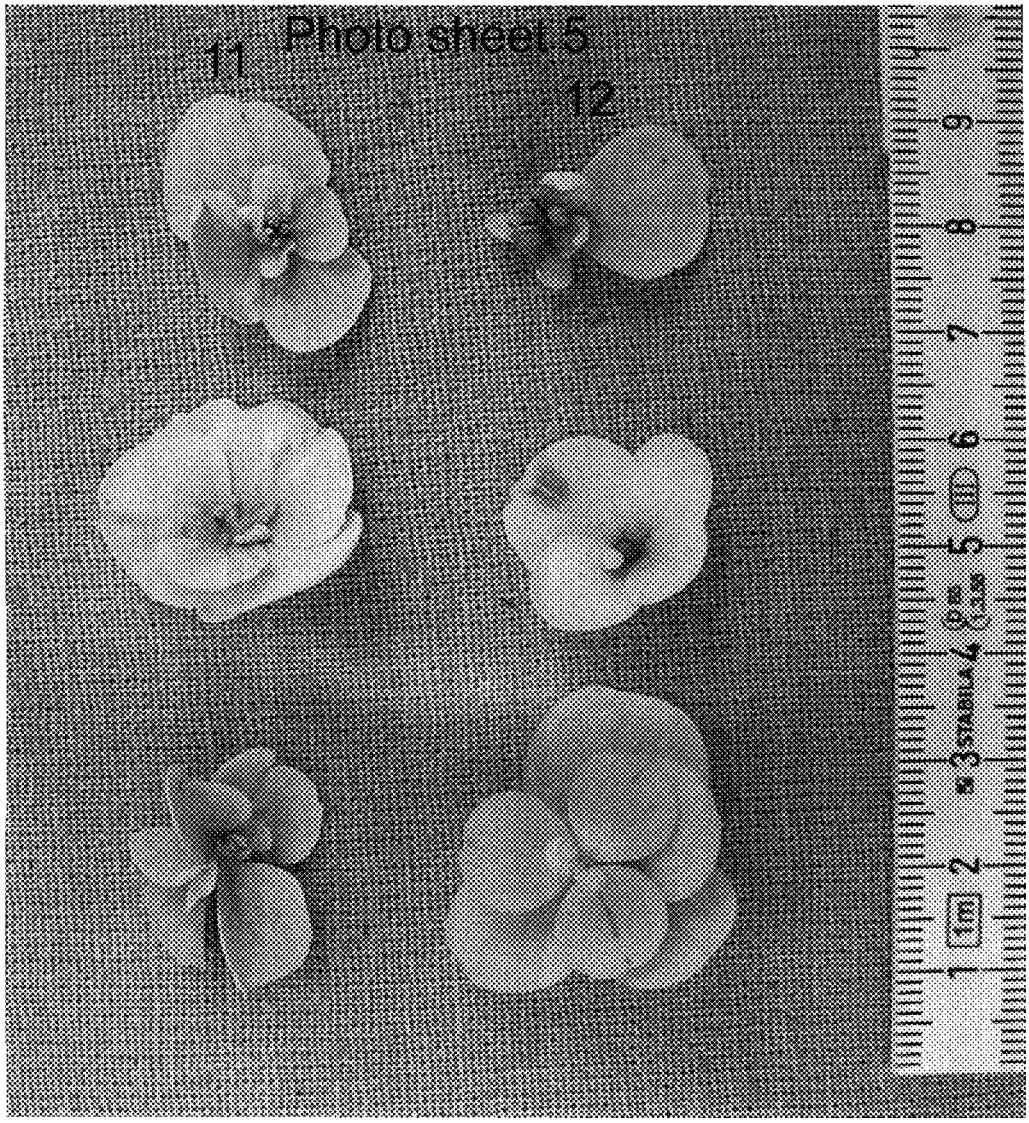
Photo sheet 5
11
12